United States Patent
Sakuta

(10) Patent No.: US 6,503,519 B1
(45) Date of Patent: Jan. 7, 2003

(54) DERMATIC COSMETIC MATERIAL

(75) Inventor: Koji Sakuta, Gunma-Ken (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 0 days.

(21) Appl. No.: 09/599,513

(22) Filed: Jun. 23, 2000

(51) Int. Cl.⁷ .............................. A61K 7/32; A61K 7/34; A61K 7/36; A61K 7/38; A61K 7/00

(52) U.S. Cl. ...................... 424/401; 424/65; 424/66; 424/67; 424/68; 514/770; 514/827; 514/828; 514/938

(58) Field of Search ................................ 424/401, 65, 66, 424/67, 68; 514/770, 827, 828, 938

(56) References Cited

U.S. PATENT DOCUMENTS

| | | | |
|---|---|---|---|
| 5,162,378 A | * 11/1992 | Guthauser | ................... 514/785 |
| 5,412,004 A | * 5/1995 | Tachibana et al. | ............ 524/27 |
| 6,103,250 A | 8/2000 | Brieva et al. | |

FOREIGN PATENT DOCUMENTS

| | | |
|---|---|---|
| JP | 09-175990 | 7/1997 |
| JP | 10-182354 | 7/1998 |

* cited by examiner

*Primary Examiner*—Frederick Krass
*Assistant Examiner*—Clinton Ostrup
(74) *Attorney, Agent, or Firm*—Millen, White, Zelano & Branigan, P.C.

(57) ABSTRACT

A dermatic cosmetic material containing as a substrate a silicone composition paste comprising (i) a cross-linked silicone polymer having hydrophilic polyoxyalkylene groups wherein polyoxyethylene moieties are comprised, which functions as a thickener component, and (ii) a silicone oil, thereby enabling stable incorporation of an antiperspirant or water-soluble vitamins and further ensuring improvements in usability.

7 Claims, No Drawings

DERMATIC COSMETIC MATERIAL

FIELD OF THE INVENTION

The present invention relates to a dermatic cosmetic material in which is mixed a paste composition comprising a three-dimensionally cross-linked silicone polymer and a silicone oil. In particular, the invention is concerned with an antiperspirant composition having characteristics that, when applied to the skin, it has neither tacky feel nor oily feel, spreads smoothly and provides a refreshing feeling to the skin, wherein are comprised an aluminum compound having an antiperspirant activity and the aforementioned paste composition. Further, the invention relates to a skin-care cosmetic material in which vitamin C is dispersed homogeneously in a stable condition owing to the incorporation of the aforementioned paste composition.

BACKGROUND OF THE INVENTION

Many antiperspirant cosmetics containing aluminum compounds as an active component in perspiration control are available. The antiperspirant compositions are used in any form of nonaqueous or aqueous liquid, solid and spray compositions.

In a case of nonaqueous liquid compositions, the foregoing active component is dispersed in oily ingredients; therefore such compositions have an oily feel. In addition, it is required to give them a good shake before their use because they cause sedimentation of the active component upon storage. Further, they have a drawback of tending to trickle down from the part to which they are applied. Then silicone oils are used as a dispersion medium for the active component with the intention of decreasing an oily feel. However, this measure cannot by itself get rid of the tendencies of the resultant compositions to deposit the active component upon storage and trickle down from the applied parts.

In another case of mixing waxy ingredients in a nonaqueous composition and forming the mixture into solid composition sticks, the sticks have a tacky feel arising from the waxy ingredients. Such a tacky feel is difficult to eliminate even when silicone oils are employed as oily ingredients. In still another case of mixing a clay mineral as thickener, e.g., montmorillonite, in a nonaqueous composition and making the resultant mixture into the creamy or gelled composition, this creamy or gelled composition cannot be rid of the tacky feel caused by the thickener. For instance, the stick composition utilizing dibenzylidene sorbitol as a gelling agent and propylene glycol as a dispersion medium has a very tacky feel. Even if it is attempted to mix silicone oils as a texture improver in the foregoing composition, the silicone oils cannot be dispersed homogeneously therein.

On the other hand, aqueous liquid compositions are prepared by dispersing the active component into water or a water-alcohol mixture. As the active component can be dissolved homogeneously in the dispersion medium, the sedimentation thereof can be prevented from occurring upon storage. However, the compositions still tend to trickle down from the applied parts.

While the aqueous compositions can be converted into creamy or gelled compositions by the use of a polyacrylic acid salt as a thickener, they are similar in drawback of having a tacky feel arising from the thickener to the foregoing nonaqueous compositions. So it has been attempted to convert the aqueous compositions into creamy compositions of oil-in-water or water-in-oil type by the use of emulsifiers. However, those compositions also have an irritant or tacky feel originating in the emulsifiers.

In the case where it is intended that various vitamins be compounded in cosmetic materials for the purpose of furnishing nutrition to the skin, water-soluble vitamin C is difficult to disperse homogeneously into the cosmetic materials in a stabilized condition. This is because the water solution of vitamin C is liable to undergo oxidative decomposition, and so it is inferior in storage stability. Even when such cosmetic materials are prepared as emulsions of oil-in-water or water-in-oil type, their storage stability problem cannot be resolved. Therefore, cases are known where the cosmetic materials are prepared as nonaqueous compositions whose dispersion medium is alcohol. When the silicone oils as texture improver are added to such compositions, however, it is difficult to obtain homogeneous dispersions.

SUMMARY OF THE INVENTION

Therefore, a first object of the invention is to provide dermatic cosmetic materials, including antiperspirant compositions in a gel state, particularly an antiperspirant composition of emulsifier-free emulsion type, which have no tacky feel arising from a thickener whether the compositions are aqueous or nonaqueous, and create comfortable feelings when applied to the skin.

A second object of the invention is to provide nonaqueous dermatic cosmetic materials of homogeneous paste type, including a vitamin C-containing skin-care cosmetic material, which contain a lower alcohol and a silicone oil as a dispersion medium and has high storage stability.

As a result of our intensive studies for attaining the aforementioned objects, it has been found that the antiperspirant composition giving a comfortable feeling to the applied skin and the vitamin C-containing skin-care composition having high storage stability can be obtained by using as a substrate a silicone composition paste comprising (i) a silicone polymer having hydrophilic polyoxyalkylene groups, wherein polyoxyethylene moieties are comprised, and a cross-linked structure and (ii) a silicone oil, thereby achieving the present invention.

Namely, the present invention provides a dermatic cosmetic material containing as a substrate a silicone composition paste comprising a silicone oil and a cross-linked silicone polymer having hydrophilic polyoxyalkylene groups in which polyoxyethylene moieties are comprised.

DETAILED DESCRIPTION OF THE INVENTION

The present silicone composition paste is a composition prepared by dispersing homogeneously in a silicone oil a cross-linked silicone polymer having hydrophilic polyoxyalkylene groups which is produced by addition polymerization reaction between an organohydrogenpolysiloxane and a compound having terminal aliphatic unsaturated groups. The organohydrogenpolysiloxane usable in this addition polymerization reaction is a hydrophilic polyoxyalkylene group-containing organohydrogenpolysiloxane represented by formula,

$$R^1_a R^2_b H_c SiO_{(4-a-b)/2} \qquad (1),$$

an organohydrogenpblysiloxane represented by formula,

$$R^1_j H_k SiO_{(4-j-k)/2} \qquad (2),$$

or a mixture of these organohydrogenpolysiloxanes; while the compound having terminal aliphatic unsaturated groups usable in this addition polymerization reaction is a polyalkylene oxide represented by formula, $$C_mH_{2m-1}(C_2H_4O)_p(C_3H_6O)_qC_mH_{2m-1} \quad (A),$$

an organopolysiloxane represented by formula, $$R^1_d R^3_e SiO_{(4-d-e)/2} \quad (B),$$

or a mixture of these compounds. Moreover, at least either the organohydrogenpolysiloxane represented by formula (1) or the polyalkylene oxide represented by formula (A) is the essential component in the aforementioned addition polymerization reaction. In those formulae, $R^1$ represents an alkyl group containing 1 to 18 carbon atoms, an aryl group, an aralkyl group or a monovalent halogenated hydrocarbon group; $R^2$ represents an organic group represented by —$C_nH_{2n}O(C_2H_4O)_f(C_3H_6O)_gR^4$; $R^3$ represents a monovalent 2–10C hydrocarbon group having a terminal vinyl group; $R^4$ represents a hydrogen atom, a 1–10C saturated organic group, or a group represented by —CO—$R^5$; $R^5$ represents a 1–5C saturated organic group; $1.0 \le a \le 2.5$, $0.001 \le b \le 1.0$, $0.001 \le c \le 1.0$, $1.0 \le d \le 3.0$, $0.001 \le e \le 1.5$, $1.0 \le j \le 3.0$, $0.001 \le k \le 1.5$; f and p are each an integer of from 2 to 200; g and q are each an integer of from 0 to 200; and m and n are each an integer of from 2 to 6. More specifically, the present silicone composition paste includes the silicone composition disclosed in Japanese Tokkai Hei 4-272932 (the term "Tokkai" as used herein means an "unexamined published patent application"), and the silicone composition disclosed in Japanese Tokkai Hei 5-140320 which is prepared by making a combination of proper compounds to synthesize a cross-linked silicone polymer having hydrophilic polyoxyalkylene groups, wherein one compound is selected from organohydrogenpolysiloxanes represented by formula (1), organohydrogenpolysiloxanes represented by formula (2) or mixtures thereof and the other compound is selected from polyalkylene oxides represented by formula (A), organopolysiloxanes represented by formula (B) or mixtures thereof, provided that at least either organohydrogen-polysiloxane of formula (1) or polyalkylene oxide of formula (A) is included in the combination, subjecting the combination to addition polymerization reaction in the presence of a low-viscosity silicone oil having a viscosity of no higher than 100 mm$^2$/s at 25° C., a polyhydric alcohol or a mixture thereof, and then dispersing the thus prepared silicone polymer into a silicone oil.

In accordance with the invention, the silicone composition paste as mentioned above is employed as a substrate (Component (A)) and combined with the following Components (B) to (F), thereby preparing a dermatic cosmetic material such as an antiperspirant composition or a skin-care composition.

Anti-perspiration active aluminum compounds usable as Component (B) are aluminum chlorohydrate and aluminum zirconium chlorohydrate. Examples of available products of such aluminum compounds include Microdry UF, REACH101, REACH103, REACH301, REACH301 SOLUTION, REACH501, REACH501 SOLUTION, REHYDOL II, REACH AZP 902, REACH AZP 908, REACH AZP 855, REACH AZZ 902, REACH AZZ 855, REACH AZN 885, REZAL 36P, REZAL 36 SOLUTION, REZAL 36GP, REZAL 36G SOLUTION, REZAL 67P and REZAL 67 SOLUTION (trade names, products of Reheis Chemical Company).

Examples of a lower alcohol usable as Component (C) include monohydric alcohols, such as ethanol and 2-propanol, and polyhydric alcohols, such as ethylene glycol, diethylene glycol, triethylene glycol, propylene glycol, dipropylene glycol, tripropylene glycol, isoproterenol and glycerine. Of these alcohols, water-soluble alcohols, especially ethanol and dipropylene glycol, are preferred in the invention.

Silicone oils usable as Component (E) are those having a viscosity of no higher than 100 mm$^2$/s at 25° C., with examples including straight-chain or branched dimethylsilicone, methylphenylsilicone and fluorine-modified silicone. In the invention, silicone oils having a viscosity of no higher than 50 mm$^2$/s are used to advantage. In particular, volatile dimethylsilicones having a boiling point of no higher than 250° C. are preferred over the others.

The present antiperspirant composition can be obtained by using as a substrate the silicone composition paste described above as Component (A), and incorporating an active component (Component (B)) as a main agent into the substrate. This antiperspirant composition is a non-aqueous composition, and assumes a creamy or gelled state. Since the thickener component in the substrate is the cross-linked silicone polymer as mentioned above, the resultant composition is free of a tacky feel and spreads smoothly.

The suitable proportion of Component (B) in the non-aqueous antiperspirant composition is from 50 to 500 parts by weight, preferably 50 to 300 parts by weight, to 100 parts by weight of Component (A). When the Component (B) is contained in a proportion smaller than 50 parts by weight, the resultant composition has little antiperspirant effect; while, when the proportion thereof is increased beyond 500 parts by weight, the resultant composition gives a heavy feel to the users thereof.

For preparing an antiperspirant composition having a transparent jelly-like appearance, it is desirable that the content of Component (B) in the composition be from 100 to 1,000 parts by weight per 100 parts by weight of Component (A), that of Component (C) be from 100 to 2,000 parts by weight per 100 parts by weight of Component (A) and that of Component (D) be from 50 to 3,000 parts by weight per 100 parts by weight of Component (A). When the content of Component (B) is lower than 100 parts by weight, the resultant composition has little antiperspirant effect; while, when it is higher than 1,000 parts by weight, the resultant composition has a heavy feel. The most suitable content of Component (B) is therefore from 100 to 500 parts by weight.

When the content of Component (C) is lower than 100 parts by weight, the resultant composition cannot have a transparent appearance; while, when it is higher than 2,000 parts by weight, the resultant composition feels tacky. In particular, it is desirable for Component (C) to be contained in a proportion of from 100 to 1,000 parts by weight. As to Component (D), when its content is lower than 50 parts by weight, the resultant composition is short of a refreshing impression; while, when its content is increased beyond 3,000 parts by weight, the resultant composition loses its transparency. Therefore, the particularly suitable content of Component (D) is from 100 to 2,000 parts by weight.

For preparing an emulsified composition of water-in-oil type, on the other hand, it is desirable that the content of Component (B) in the composition be from 100 to 2,000 parts by weight per 100 parts by weight of Component (A) and that of Component (D) be from 50 to 5,000 parts by weight per 100 parts by weight of Component (A). When the content of Component (B) is lower than 100 parts by weight, the resultant composition has little antiperspirant effect; while, when it is increased beyond 2,000 parts by weight, the resultant composition feels heavy. In such a type of composition, therefore, the preferable content of Component (B) is from 100 to 1,000 parts by weight. As to Component (D), when its content is lower than 50 parts by weight, the resultant composition is short of a refreshing feeling; while, when its content is increased beyond 5,000 parts by weight, the emulsion obtained loses its stability. Therefore, the preferable content thereof is from 100 to 3,000 parts by weight.

In addition to those components, the ingredients which has so far been used in conventional antiperspirants, such as oils including silicone oil, ester oil and hydrocarbon oil, higher alcohols including cetyl alcohol and stearyl alcohol, and perfume, may further be mixed in the present composition.

In the case of preparing a skin-care composition containing vitamin C, it is desirable that the content of Component (C) be from 100 to 1,000 parts by weight per 100 parts by weight of Component (A), that of Component (E) be from 100 to 1,000 parts by weight per 100 parts by weight of Component (A) and that of vitamin C be from 0.5 to 100 parts by weight per 100 parts by weight of Component (A).

When the content of Component (C) is lower than 100 parts by weight, the resultant composition is short of compatibility with vitamin C; while, when it is higher than 1,000 parts by weight, the resultant composition cannot does not feel comfortable. Therefore, the preferable content of Component (C) is from 100 to 500 parts by weight. As to Component (E), when its content is lower than 100 parts by weight, the resultant composition does not feel comfortable; while, when its content is increased beyond 1,000 parts by weight, the resultant composition is not in a paste state. Therefore, the preferable content of Component (E) is from 100 to 500 parts by weight.

When the content of vitamin C is lower than 0.5 parts by weight, the resultant composition has little skin-care effect; while, when it is increased beyond 100 parts by weight, it becomes difficult to prepare a homogeneous dispersion. Therefore, the especially desirable content of vitamin C is from 0.5 to 50 parts by weight.

Besides the foregoing components, the ingredients usable for general skin-care cosmetics, such as oils including ester oil and hydrocarbon oil, higher alochols including cetyl alcohol and stearyl alcohol, perfume and vitamins including vitamins A, B, D, E, F, K, L, T and U, may be mixed in the present skin-care composition.

In accordance with the present invention, the antiperspirant composition obtained has neither tacky feel nor oily feel, but can spread smoothly and create a refreshing feeling in the users. And the skin-care composition obtained has excellent storage stability and can give comfortable feelings to the users. In other words, the dermatic cosmetic materials according to the present invention have significant improvements over conventional ones.

Now, the present invention will be illustrated in greater detail by reference to the following examples. However, the invention should not be construed as being limited to these examples. Additionally, the silicone composition paste used as a substrate is prepared using the silicone polymer synthesized in the following Synthesis Example 1.

The entire disclosure of all applications, patents and publications, cited above and below, and of corresponding Japanese application No. Hei 11-177904, filed, Jun. 24, 1999, is hereby incorporated by reference.

SYNTHESIS EXAMPLE 1

In a reaction vessel were placed 100 g of organohydrogenpolysiloxanes represented by the following average structural formula,

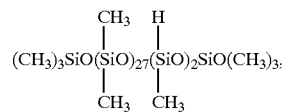

103.0 g of ethanol, 23.6 g of polyoxyalkylene represented by the following average structural formula,

and 0.3 g of a 3 weight % ethanol solution of chloroplatinic acid. The contents in the reaction vessel were stirred for 2 hours while keeping the temperature thereof at 70–80° C., and then the solvent was removed under reduced pressure. Thus, a silicone polymer was obtained.

A 100 parts by weight portion of the silicone polymer thus obtained was mixed with 300 parts by weight of dimethylpolysiloxane having the viscosity of 6 mm$^2$/s at 25° C., and further kneaded by means of a three-rod roll mill to prepare a silicone composition in a paste state (Silicone Composition No. 1).

Another 100 parts by weight portion of the silicone polymer obtained was mixed with 400 parts by weight of decamethylcyclopentasiloxane, and further kneaded with a three-rod roll mill to prepare a silicone composition in a paste state (Silicone Composition No. 2).

EXAMPLES 1 TO 3

Nonaqueous Antiperspirant Compositions:

Nonaqueous antiperspirant samples having the compositions shown in Table 1 were prepared.

TABLE 1

| | Proportions of ingredients mixed (weight %) | | |
|---|---|---|---|
| Ingredients mixed | Example 1 | Example 2 | Example 3 |
| Silicone Composition 1 | 20.0 | 20.0 | 0 |
| KSG15*[1] | 0 | 20.0 | 0 |
| Silicone Composition 2 | 0 | 0 | 30.0 |
| Decamethylcyclopentasiloxane | 40.0 | 30.0 | 50.0 |
| Dimethylpolysiloxane (viscosity: 6 mm$^2$/s) | 20.0 | 0 | 0 |
| Propylene glycol | 0 | 10.0 | 0 |
| Aluminum zirconium compound*[2] | 20.0 | 20.0 | 20.0 |

*[1] A hydrophobic composition paste prepared from a dispersion of cross-linked polymer of methylhydrogenpolysiloxane and methylvinylpolysiloxane in decamethylpentasiloxane (produced by SHIN-ETSU CHEMICAL Co., Ltd.).
*[2] REZAL 36GP Superultrafine (trade name, a product of Reheis Chemical Company).

Each of the thus obtained roll-on antiperspirant samples spread smoothly, gave a refreshing feeling, had neither tacky nor oily feel, and caused no change by temperature and aging. In other words, the antiperspirants according to the invention had excellent usability and stability.

EXAMPLES 4 TO 6

Transparent Antiperspirant Compositions in Gel State:

Transparent antiperspirant gel samples having the compositions shown in Table 2 were prepared.

TABLE 2

| Ingredients mixed | Proportions of Ingredients mixed (weight %) | | |
|---|---|---|---|
| | Example 4 | Example 5 | Example 6 |
| Silicone Composition 1 | 8.0 | 5.0 | 0 |
| Silicone Composition 2 | 0 | 0 | 10.0 |
| Decamethylcyclopentasiloxane | 12.0 | 10.0 | 20.0 |
| Dipropylene glycol | 16.0 | 0 | 16.0 |
| Propylene glycol | 0 | 15.0 | 0 |
| Aluminum zirconium compound*[3] | 20.0 | 20.0 | 20.0 |
| Ion-exchange water | 44.0 | 60.0 | 34.0 |

*[3]REZAL 36GP (trade name, a product of Reheis Chemical Company)

Each of the thus obtained transparent antiperspirant gel samples spread smoothly, gave a refreshing feeling, had neither tacky nor oily feel, and caused no change by temperature and aging. In other words, the transparent antiperspirant gel according to the invention had excellent usability and stability.

EXAMPLES 7 TO 9
Antiperspirant Compositions of Water-in-Oil Emulsion Type:

Water-in-oil emulsion type of antiperspirant samples having the compositions shown in Table 3 were prepared.

TABLE 3

| Ingredients mixed | Proportions of Ingredients mixed (weight %) | | |
|---|---|---|---|
| | Example 7 | Example 8 | Example 9 |
| Silicone Composition 1 | 20.0 | 4.0 | 0 |
| Silicone Composition 2 | 0 | 0 | 10.0 |
| Decamethylcyclopentasiloxane | 7.0 | 8.0 | 20.0 |
| Dimethylpolysiloxane (viscosity: 6 mm$^2$/s) | 0 | 2.0 | 0 |
| Glycerin trioctanate | 10.0 | 0 | 0 |
| 1,3-butylene glycol | 5.0 | 5.0 | 0 |
| Glycerin | 0 | 0 | 5.0 |
| Sodium citrate | 0.3 | 0.3 | 0.3 |
| Aluminum zirconium compound*[4] | 20.0 | 20.0 | 20.0 |
| Ion-exchange water | 50.7 | 60.7 | 44.7 |

*[4]REACH (trade name, a product of Reheis Chemical Company)

Each of the thus obtained antiperspirant samples of water-in-oil emulsion type spread smoothly, gave a refreshing feeling, had neither tacky nor oily feel, and caused no change by temperature and aging. In other words, the antiperspirant emulsions according to the invention had excellent usability and stability.

EXAMPLES 10 TO 12
Skin-care Compositions Containing Vitamin C:

Vitamin C-containing skin-care compositions constituted of the ingredients shown in Table 4 were prepared.

TABLE 4

| Ingredients mixed | Proportions of Ingredients mixed (weight %) | | |
|---|---|---|---|
| | Example 10 | Example 11 | Example 12 |
| Silicone Composition 1 | 20.0 | 0 | 30.0 |
| Silicone Composition 2 | 0 | 30.0 | 0 |
| Decamethylcyclopentasiloxane | 40.0 | 30.0 | 47.0 |
| Dimethylpolysiloxane (viscosity: 6 mm$^2$/s) | 0 | 5.0 | 0 |
| Dipropylene glycol | 38.0 | 0 | 20.0 |
| 1,3-butylene glycol | 0 | 32.0 | 0 |
| Cetyl alcohol | 0 | 1.0 | 0 |
| Vitamin C | 2.0 | 1.0 | 2.0 |
| Vitamin E | 0 | 1.0 | 1.0 |

Each of the thus prepared vitamin C-containing skin-care compositions spread smoothly, gave a refreshing feeling, had neither tacky nor oily feel, and caused no change by temperature and aging. In other words, the skin-care compositions according to the invention had excellent usability and stability despite the incorporation of vitamin C therein.

What is claimed is:

1. An antiperspirant dermatic cosmetic material in a transparent gel state, comprising:
   (A) 100 parts by weight of a silicone composition paste comprising (i) a cross-linked silicone polymer having hydrophilic polyoxyalkylene groups wherein polyoxyethylene moieties are comprised and (ii) a silicone oil,
   (B) 100 to 1,000 parts by weight of an aluminum compound having a perspiration control activity,
   (C) 100 to 2,000 parts by weight of lower alcohol, and
   (D) 50 to 3,000 parts by weight of water.

2. An antiperspirant dermatic cosmetic material according to claim 1, wherein the silicone polymer is a polymer produced by carrying out addition polymerization reaction of a hydrophilic polyoxyalkylene group-containing organohydrogenpolysiloxane, an organohydrogenpolysiloxane or a mixture thereof with a hydrophilic polyalkylene oxide having terminal aliphatic unsaturated groups, an organopolysiloxane having terminal aliphatic unsaturated groups or a mixture thereof, provided that at least either the hydrophilic polyoxyalkylene group-containing organohydrogenpolysiloxane or the polyalkylene oxide is a reactant in the addition polymerization reaction.

3. An antiperspirant dermatic cosmetic material according to claim 1, wherein the aluminum compound is an aluminum chlorohydrate or an aluminum zirconium chlorohydrate.

4. An antiperspirant dermatic cosmetic material according to claim 1, comprising 50 to 300 parts by weight of an aluminum compound.

5. An antiperspirant dermatic cosmetic material according to claim 1, wherein the lower alcohol is ethanol, 2-propanol, ethylene glycol, diethylene glycol, triethylene glycol, polpylene glycol, dipropylene glycol, tripropylene glycol, isoproterenol, or glycerine.

6. An antiperspirant dermatic cosmetic material according to claim 1, comprising 100 to 500 parts by weight of the lower alcohol.

7. An antiperspirant dermatic cosmetic material according to claim 1, wherein the antiperspirant dermatic cosmetic material is emulsifier-free.

* * * * *